United States Patent
Volz et al.

(10) Patent No.: US 8,722,682 B2
(45) Date of Patent: May 13, 2014

(54) SULFATED BENZIMIDAZOLONE DERIVATIVES HAVING MIXED SEROTONIN RECEPTOR AFFINITY

(75) Inventors: Astrid Volz, Ingelheim am Rhein (DE); Ralf Lotz, Schemmerhofen (DE); Fabio Paleari, Monza (IT)

(73) Assignee: Sprout Pharmaceuticals, Inc., Raleigh, NC (US)

( * ) Notice: Subject to any disclaimer, the term of this patent is extended or adjusted under 35 U.S.C. 154(b) by 458 days.

(21) Appl. No.: 12/518,574

(22) PCT Filed: Dec. 18, 2007

(86) PCT No.: PCT/EP2007/064120
§ 371 (c)(1),
(2), (4) Date: Oct. 4, 2010

(87) PCT Pub. No.: WO2008/074795
PCT Pub. Date: Jun. 26, 2008

(65) Prior Publication Data
US 2011/0015207 A1    Jan. 20, 2011

(30) Foreign Application Priority Data
Dec. 20, 2006    (EP) ..................... 06126689

(51) Int. Cl.
A61K 31/496    (2006.01)
C07D 235/26    (2006.01)

(52) U.S. Cl.
USPC ..................... 514/254.06; 544/370

(58) Field of Classification Search
None
See application file for complete search history.

(56) References Cited

U.S. PATENT DOCUMENTS

| | | | |
|---|---|---|---|
| 5,576,318 | A | 11/1996 | Bietti et al. |
| 6,083,947 | A | 7/2000 | Granger et al. |
| 6,521,623 | B1 | 2/2003 | Cereda et al. |
| 6,586,435 | B2 | 7/2003 | Cereda et al. |
| 7,151,103 | B2 | 12/2006 | Borsini et al. |
| 7,183,410 | B2 | 2/2007 | Bombarda et al. |
| 7,420,057 | B2 | 9/2008 | Bombarda et al. |
| 7,923,449 | B2 | 4/2011 | Ceci |
| 8,227,471 | B2 | 7/2012 | Borsini et al. |
| 8,227,476 | B2 | 7/2012 | Ceci et al. |
| 2002/0160042 | A1 | 10/2002 | Petereit et al. |
| 2003/0060475 | A1 | 3/2003 | Borsini |
| 2003/0119850 | A1 | 6/2003 | Bombarda et al. |
| 2004/0193452 | A1 | 9/2004 | Berman |
| 2005/0065158 | A1 | 3/2005 | Naylor et al. |
| 2005/0095293 | A1 | 5/2005 | Brauns et al. |
| 2005/0239798 | A1 | 10/2005 | Pyke |
| 2005/0245539 | A1 | 11/2005 | Mendla et al. |
| 2006/0264511 | A1 | 11/2006 | Pyke |
| 2007/0032655 | A1 | 2/2007 | Bombarda et al. |
| 2007/0196473 | A1 | 8/2007 | Friedl et al. |
| 2008/0038347 | A1 | 2/2008 | Eisenreich et al. |
| 2008/0275082 | A1 | 11/2008 | Brum et al. |
| 2009/0022797 | A1 | 1/2009 | Rossi et al. |
| 2011/0015207 | A1 | 1/2011 | Volz et al. |
| 2011/0136825 | A1 | 6/2011 | Hanes et al. |
| 2012/0035185 | A1 | 2/2012 | Borsini |
| 2012/0122883 | A1 | 5/2012 | Mazurek et al. |
| 2012/0270883 | A1 | 10/2012 | Bombarda et al. |
| 2013/0172304 | A1 | 7/2013 | Boeck |
| 2013/0203671 | A1 | 8/2013 | Castro et al. |
| 2013/0203766 | A1 | 8/2013 | Mendla et al. |

FOREIGN PATENT DOCUMENTS

| | | |
|---|---|---|
| AU | 2006311038 B2 | 1/2013 |
| EP | 0 526 434 A1 | 2/1993 |
| EP | 1 256 343 A1 | 11/2002 |
| EP | 1 285 658 A2 | 2/2003 |
| EP | 1 948 177 B1 | 8/2011 |
| EP | 1 322 622 B1 | 10/2012 |
| WO | 01/00224 A1 | 1/2001 |
| WO | 01/21593 A1 | 3/2001 |
| WO | 03/007949 A1 | 1/2003 |
| WO | 03/014079 A1 | 2/2003 |
| WO | 03/035072 A1 | 5/2003 |
| WO | 03/074032 A1 | 9/2003 |
| WO | 03/097058 A1 | 11/2003 |

(Continued)

OTHER PUBLICATIONS

Kroll J.Reprod.Med. vol. 51(4),pp. 359-370 (2006) (Abstract provided).*

(Continued)

*Primary Examiner* — Emily Bernhardt
(74) *Attorney, Agent, or Firm* — Additon, Higgins, Pendleton & Ashe, P.A.

(57) ABSTRACT

The present invention pertains to a compound of formula (I)

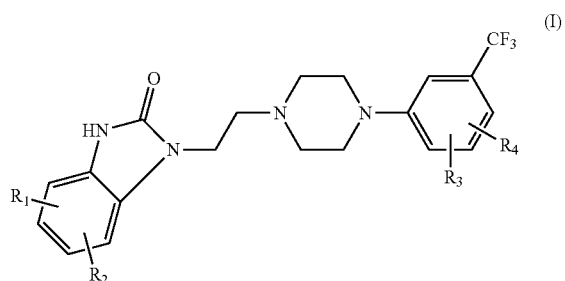

wherein $R_1$, $R_2$, $R_3$, and $R_4$ are each hydrogen or sulfate monoester with the proviso that $R_1$, $R_2$, $R_3$, and $R_4$ cannot simultaneously be hydrogen, processess for their preparation and their use as pharmaceuticals in the treatment of CNS disorders.

6 Claims, No Drawings

(56) References Cited

FOREIGN PATENT DOCUMENTS

| WO | 20041041259 A1 | 5/2004 |
|---|---|---|
| WO | 20051007166 A1 | 1/2005 |
| WO | 20051102342 A1 | 11/2005 |
| WO | 20051102343 A1 | 11/2005 |
| WO | 20071014929 A1 | 2/2007 |
| WO | 20081006838 A1 | 1/2008 |
| WO | 2008-019996 A2 | 2/2008 |
| WO | 2008-022932 A2 | 2/2008 |
| WO | 2008-116890 A2 | 10/2008 |

OTHER PUBLICATIONS

Kaur et al. Cleveland Clinic Journal of Medicine.vol. 71(4),pp. 303-321 (2004).*
Flibanserin, from Wikipedia, 6 pages,retrieved from the Internet at http://en.wikipedia.org/wiki/Flibanserin on Jul. 3, 2012.*
Berge et al.; Pharmaceutical Salts; Journal of Pharmaceutical Sciences; Jan. 1977; vol. 66, No. 1; pp. 1-19.
Borsini et al.; Flibanserin; Drugs of the Future; 1998, 23(1); pp. 9-16.
Cremers et al.; Non Erectile Dysfunction Application of Sildenafil; Herz, 2003; 28, No. 4; pp. 325-333.
Fourcroy; Female Sexual Dysfunction, Potential for Pharmacotherapy; Drugs 2003; 63 (14) pp. 1445-1457.
Hancock et al.; What is the True Solubility Advantage for Amorphous Pharmaceuticals; Pharmaceutical Research, vol. 17, No. 4; 2000; pp. 397-404.
Kumar et al.; an overview of automated systems relevant in pharmaceutical salt screening; Drug Discovery Today, vol. 12, Nos. 23/24, Dec. 2007; pp. 1046-1053.
Molinoff et al.; PT-141: A Melanocortin Agonist for the Treatment of Sexual Dysfunction; Annals New York Academy of Sciences; 994; 2003; pp. 96-102.
Quirk et al.; Development of a Sexual Function Questionnaire for Clinical Trails of Female Sexual Dysfunction; Journal of Women's Health & Gender-Based Medicine, vol. 11, No. 3; 2002; pp. 277-289.
Rosen et al.; The Female Sexual Function Index (FSFI): A Multidimensional Self-Report Instrument for the Assessment of Female Sexual Function; Journal of Sex & Marital Therapy, 26:191-208, 2000.
Salon Ia et al.; Sexual Dysfunction is Common in Women with Lower Urinary Tract Symptoms and Urinary Incontinence: Results of a Cross-Sectional Study; European Urology 45, 2004; pp. 642-648.
Stahl et al.; Handbook of Pharmaceutical Salts Properties, Selection, and Use; pp. 211-217; International Union of Pure and Applied Chemistry (IUPAC) date unknown.
Tanaka et al.; B3-Adrenoceptor Agonists for the Treatment of Frequent Urination and Urinary Incontinence: 2-[4-2{[1S,2R)-2-Hydroxy-2-(4-hydroxyphenyl)-1-methylethyl]amino}ethyl)phenoxy]-2-methylpropionic Acid; Bioorganic & Medicinal Chemistry 9 (2001); 3265-3271.
Response filed Feb. 17, 2012 in counterpart European Patent Application No. 09774901.4; 7 pages.
Response filed Apr. 17, 2012 in counterpart European Patent Application No. 07728833.0; 19 pages.
Response filed Aug. 27, 2012 in counterpart Australian Patent Application No. 2006311038; 16 pages.
Response filed Sep. 12, 2012 in counterpart Australian Patent Application No. 2007247094; 23 pages.
Response filed Sep. 6, 2012 in counterpart European Patent Application No. 07787338.8; 4 pages.
Albertazzi; Noradrenergic and serotonergic modulation to treat vasomotor symptoms; J. Br. Menopause Soc., Mar. 12, 2006; (1) 7-11; Abstract.
Berman et al.; Safety and Efficacy of Sildenafil Citrate for the Treatment of Female Sexual Arousal Disorder: A Double-blind, Placebo Controlled Study; The Journal of Urology; Dec. 2003; vol. 170, pp. 2333-2338.
Flibanserin, from Wikipedia, 6 pages, retrieved from the Internet at http://en.wikipedia.org/wiki/Flibanserin on Jul. 3, 2012.
Ghizzani, et al.; Management of Sexual Dysfunctions in Women; J. Endorinol. Invest. 26 (Suppl to No. 3): 2003; pp. 137-138.
Kaur, et al.; Prementrual Dysphoric Disorder: a Review for the Treating Practitioner; Cleveland Clinic Journal of Medicine, vol. 71, No. 4, Apr. 2004; pp. 303-321.
Kroll, Treatment of Premenstrual Disorders, J. Reprod. Med., Apr. 2006; (4 Suppl)—Abstract.
Lachman et al.; The Theory and Practice of Industrial Pharmacy, 3rd Edition, Lea and Febiger Philadelphia, 1986, pp. 324-333.
Salerian et al.; Sildenafil for Psychotropic-Induced Sexual Dysfunction in 31 Women and 61 Men; Journal of Sex & Marital Therapy; 2000, 26:2, pp. 133-140.
Sietsema et al.; From Taboo to Treatment?; 2005 PJB Publications, Jan. 2005; pp. 23-27.
Walsh et al.; Sexual Dysfunction in the Older Woman, An Overview of the Current Understanding and Management; Drugs Aging 2004; 21 (10); pp. 656-675.
Response filed Dec. 19, 2012 in counterpart European Patent Application No. 06764270.2; 26 pages.
Semkova et al., Neuroprotective effect of 5-HT1A receptor agonist, Bay x 3702, demonstrated in vitro and in vivo, 1998, European Journal of Pharmacology, vol. 359, pp. 251-260.
Prehn et al., Neuroprotective properties of 5-HT1A receptor agonists in rodent models of focal and global cerebral ischemia, 1991, European Journal of Pharmacology, vol. 203, pp. 213-222.
Elger et al., Oedema reduction by levemopamil in focal cerebral ischemia of spontaneously hypertensive rats studied by magnetic resonance imaging, 1994, European Journal of Pharmacology, vol. 254, pp. 65-71.
Borsini et al., Bimt 17: a putative antidepressant with a fast onset of action?, 1997, Psychopharmacology, vol. 134, pp. 378-386.
Response filed Jan. 25, 2013 in counterpart Canadian Patent Application No. 2,617,546; 17 pages.
Response filed Feb. 7, 2013 in counterpart Canadian Patent Application No. 2,563,743; 15 pages.
Response filed Feb. 20, 2013 in counterpart Canadian Patent Application No. 2,626,134; 7 pages.
Response filed Feb. 20, 2013 in counterpart Canadian Patent Application No. 2,626,797; 8 pages.
Poster, presented Nov. 6, 2009 at Sexual Medicine Society of North American 2009 Fall Scientific Meeting, 3 pages.
Transcript of Poster, presented Nov. 6, 2009 at Sexual Medicine Society of North American 2009 Fall Scientific Meeting, "Pooled Clinical Trial Analysis of Flibanserin Safety and Tolerability in Premenopausal Women with Hypoactive Sexual Desire Disorder", 7 pages.
Response filed Nov. 6, 2013 in commonly owned Canadian Patent Application No. 2,649,938; 9 pages.
Response filed Nov. 6, 2013 in commonly owned Canadian Patent Application No. 2,654,798; 6 pages.
Response filed Sep. 23, 2013 in commonly owned Canadian Patent Application No. 2,617,546; 14 pages.
Response filed May 8, 2013 to Restriction Requirement dated Feb. 8, 2013 in U.S. Appl. No. 13/550,062; 5 pages.
Response filed Jun. 19, 2013 in commonly owned European Patent Application No. 07728833.0; 33 pages.

* cited by examiner

SULFATED BENZIMIDAZOLONE DERIVATIVES HAVING MIXED SEROTONIN RECEPTOR AFFINITY

This application is the national phase entry under 35 U.S.C. §371 of International Application No. PCT/EP2007/064120, filed Dec. 18, 2007, which claims priority to European Application No. 06126689, filed Dec. 20, 2006, each of which is hereby incorporated by reference in its entirety.

The present invention relates to novel pharmacologically active benzimidazolone derivatives and their addicton salts which bind the serotonine and dopamine receptors, to their preparation and their use for therapeutic purposes. These compounds, owing to their pharmacological activity, are useful in the treatment of CNS disorders.

BACKGROUND OF THE INVENTION

Serotonine (5-HT) recognises several well defined cell surface receptors. Among these, 5-$HT_{1A}$ and 5-$HT_{2A}$ at which serotonine have high affinity, are known to be implicated in many Central Nervous System disorders such as sexual disorders, depression, anxiety, schizophrenia, Parkinson and neurodegenerative diseases (EP 0 526 434 B1; WO 01/21593 A1; WO 02/24661 A2; WO 02/24662 A1; WO 03/014079 A1; WO 03/013539 A1; WO 03/035072 A1; WO 05/102343 A1; WO 06/019715 A1; WO 06/010574 A1; WO 06/024471 A1.

In the previous art, several classes of compounds able to interfere with the neurotransmission at serotonine or dopamine receptor subtypes are known. Particularly, derivatives based on the core structure of the arylpiperazine and benzimidazolone have been described (e.g. GB 2023594, U.S. Pat. Nos. 3,472,854, 4,954,503 and WO 98/33784), and targeted both to generic serotonine or dopamine receptors and to a specific receptor subtype. In another patent (U.S. Pat. No. 5,576,318) compounds based both on the benzimidazolone and phenyl piperazine structures are described: in this latter case the described affinities are limited to 5-$HT_{1A}$ and 5-$HT_{2A}$ receptor subtypes. Further compounds with affinity to 5-HT recptors and their synthesis have been disclosed in WO 01/21593 A1.

DETAILED DESCRIPTION OF THE INVENTION

Here we describe, and this is one object of the present invention, new sulfate esters based on the benzimidazolone phenyl piperazine structure. Surprisingly it was discovered that the compounds according to this invention possess an interesting affinity profile at the said serotonine receptor subtypes: indeed, some of them have a high and preferential affinity at a given site (e.g. 5-$HT_{1A}$ or 5-$HT_{2A}$).

Owing to their peculiar profile, the present compounds may play a role in the regulation of neurotransmission at the serotonine sites and thus may be of value in the treatment of those diseases where an altered functioning of neurosignal transmission is present. Examples of these CNS disorders include depression, schizophrenia, Parkinson, anxiety, sleep disturbances, sexual and mental disorders and age associated memory impairment.

According to the present invention, we provide compounds of general formula (I)

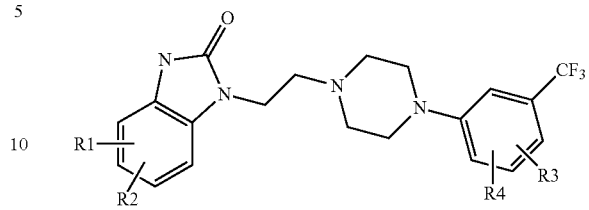

wherein
$R_1$, $R_2$, $R_3$, and $R_4$ denote hydrogen or sulfate monoester with the proviso that $R_1$, $R_2$, $R_3$, and $R_4$ cannot simultaneously represent hydrogen.

Preferred compounds according to the invention are those of general formula (I) wherein two or three of the four radicals $R_1$, $R_2$, $R_3$, and $R_4$ denote hydrogen.

Also preferred are compounds of general formula (I) wherein one of the radicals $R_1$, $R_2$, $R_3$, and $R_4$ denotes sulfate, whilst the other radicals represent hydrogen.

Of particular interest are compounds selected from the group consisting of:

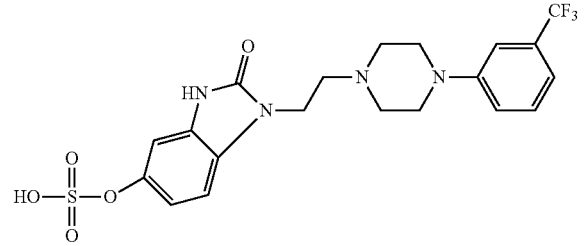
(I.a)

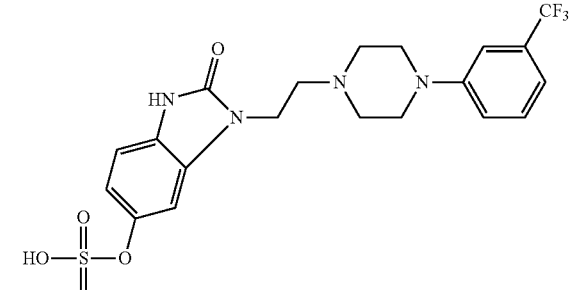
(I.b)

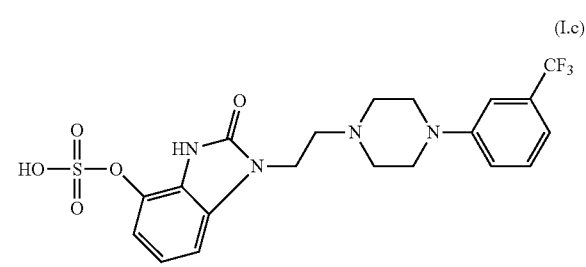
(I.c)

(I.d), (I.e), (I.f), (I.g), (I.h), (I.i), (I.j), (I.k), (I.l)

It is understood that the compounds represented by formula (I) may exist also as the corresponding zwitter ion form and that while both forms are included within the meaning of the structural formula, for simplicity sake, only the free acid form is shown.

For the pharmaceutical use the compounds of general formula (I) may be used also in the form of pharmacologically acceptable salts. As used herein, "acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic base salts of acidic residues such as sulfuric acid monoesters and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, gluconic, isethionic, glycinic, mucoic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like. Suitable base salts are formed from bases which form non-toxic salts and examples are the lithium, sodium, potassium, aluminium, calcium, magnesium, zinc, ethylamine, diethylamine, ethylenediamine, ethanolamine, diethanolamine, piperazine, choline, arginine, glycine, procaine, tromethamine, benzathine, lysine and meglumine salts (also see Pharmaceutical salts, Berge, S. M. et al., J. Pharm. Sci., (1977), 66, 1-19).

The pharmacologically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

The phrase "pharmacologically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In the light of the pharmaceutical efficacy of the compounds of formula (I), the present invention furthermore relates to the use of those compounds as a medicament.

A further aspect of the present invention relates to the use of compounds of formula (I), optionally in form of the pharmacologically acceptable salts thereof for preparing a pharmaceutical composition for treating diseases in which the use of compounds displaying affinity for the $5\text{-HT}_{1A}$, and $5\text{-HT}_2$-receptor may have a therapeutic benefit.

In a preferred embodiment, the present invention relates to the use of the one or more compounds of formula (I) selected from the group consisting of compound (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for treating diseases in which the use of compounds displaying affinity for the $5\text{-HT}_{1A}$ and $5\text{-HT}_2$-receptor may have a therapeutic benefit.

In a further embodiment the present invention relates to the use of one or more of the compounds of formula (I), more preferably to the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of sexual disorders.

The generic term "Sexual disorders" includes Sexual Desire Disorders (i.e. Hypoactive Sexual Desire Disorder, Sexual Aversion Disorder), Sexual Arousal Disorders (i.e. Female Sexual Arousal Disorder, Male Erectile Disorder), Orgasmic Disorders (i.e. Female Orgasmic Disorder, Male Orgasmic Disorder, Premature Ejaculation) Sexual Pain Disorders (i.e. Dyspareunia, Vaginismus), Sexual Dysfunction due to a General Medical Condition, Substance-Induced Sexual Dysfunction, and Sexual Dysfunction not otherwise specified (Diagnostic and Statistical Manual of Mental Disorders, 4th edition, Text Revision. Washington D.C., American Psychiatric Association, 2000).

In a preferred embodiment, the present invention relates to the use of one or more of the compounds of formula (I), more preferably to the use of one or more compounds of formula (I.a), (I.b), (I.c), (I.d), (I.e), (I.f), (I.g), (I.h), (I.f), (I.j), (I.k) and (I.l), most preferably the use of the compound of formula (I.b), optionally in form of the pharmacologically acceptable salts thereof for the preparation of a medicament for the treatment of sexual desire disorders which are a subgroup of sexual disorders.

In another preferred embodiment the invention relates to the use of one or more of the compounds of formula (I), more preferably to the use of one or more compounds of formula (I.a), (I.b), (I.c), (I.d), (I.e), (I.f), (I.g), (I.h), (I.f), (I.j), (I.k) and (I.l), most preferably the use of the compound of formula (I.b), optionally in form of the pharmacologically acceptable salts thereof for the preparation of a medicament for the treatment of disorders selected from the group consisting of hypoactive sexual desire disorder (HSDD), sexual aversion disorder, loss of sexual desire, lack of sexual desire, decreased sexual desire, inhibited sexual desire, loss of libido, libido disturbance, and frigidity.

Further preferred according to the invention is the use of one or more of the compounds of formula (I), more preferably the use of one or more compounds of formula (I.a), (I.b), (I.c), (I.d), (I.e), (I.f), (I.g), (I.h), (I.f), (I.j), (I.k) and (I.l), most preferably the use of the compound of formula (I.b), optionally in form of the pharmacologically acceptable salts thereof for the preparation of a medicament for the treatment of disorders selected from the group consisting of hypoactive sexual desire disorder (HSDD), sexual aversion disorder, loss of sexual desire, lack of sexual desire, decreased sexual desire, inhibited sexual desire.

In a more preferred embodiment the invention relates to the use of one or more of the compounds of formula (I), more preferably to the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of disorders selected from the group of hypoactive sexual desire disorder (HSDD), decreased sexual desire and inhibited sexual desire.

The observed effects of the compounds of formula (I) and the compounds (I.a), (I.b), (I.c), (I.d), (I.e), (I.f), (I.g) and (I.h), (I.i), (I.j), (I.k) and (I.l), most preferably the use of the compound of formula (I.b), optionally in form of the pharmacologically acceptable salts thereof can be achieved in men and women. However, according to a further aspect of the invention the use of the compounds of formula (I) and the compounds (I.a), (I.b), (I.c), (I.d), (I.e), (I.f), (I.g) and (I.h), (I.i), (I.j), (I.k) and (I.l), most preferably the use of the compound of formula (I.b), optionally in form of the pharmacologically acceptable salts for the preparation of a medicament for the treatment of female sexual desire disorders is preferred.

Another object of the present invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of premenstrual disorders.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of premenstrual disorders selected from the group consisting of premenstrual dysphoria, premenstrual syndrome, premenstrual dysphoric disorder.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of sexual arousal disorder in females.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of male erectile disorder.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of orgasmic disorder in females.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of orgasmic disorder in males.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of premature ejaculation in males.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), most preferably the use of the compound of formula (I.b), optionally in form of the pharmacologically acceptable salts thereof for the preparation of a medicament for the treatment of sexual pain disorders in females and males.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment sexual pain disorders selected from the group consisting of dyspareunia in females and males, vaginismus in females, and noncoital sexual pain disorder in females and males.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of, sexual dysfunction due to a general medical condition in females and males.

Further preferred according to the invention is the use of one or more of the compounds of formula (I), more preferably the use of one or more compounds of formula (I.a), (I.b), (I.c), (I.d), (I.e), (I.f), (I.g), (I.h), (I.i), (I.j), (I.k) and (I.l), most preferably the use of the compound of formula (I.b), optionally in form of the pharmacologically acceptable salts thereof for the preparation of a medicament for the treatment of substance-induced sexual dysfunction in females and males.

The beneficial effects of the compounds of formula (I) can be observed regardless of whether the above mentioned sexual disorders existed lifelong or was acquired, is of the "generalized type" or "situational type" and independent of etiologic origin (organic—both, physically and drug induced—, psychogen (due to psychological factors), a combination of organic—both, physically and drug induced—, and psychogen (due to combined factors), or unknown) origin. The term "lifelong" refers to such sexual disorders of the present invention, which have been present since the onset of sexual functioning. The term "acquired" refers to such sexual disorders of the present invention which developed only after a period of normal sexual functioning. The "generalized type" refers to such sexual disorders of the present invention wherein the disorder is not limited to certain types of stimulation, situations, or partners. The "situational type" applies to such sexual disorders of the present invention wherein the disorder is limited to certain types of stimulation, situations, or partners. The subtype due to "psychological factors" applies when psychological factors are judged to have the major role in the onset, severity, exacerbation, or maintenance of the Sexual Disorder, and general medical conditions and substance play no role in the etiology of the sexual disorder. Finally the subtype due to "combined factors" applies when 1) psychological factors are judged to have a role in the onset, severity, exacerbation, or maintenance of the sexual disorder, and 2) a general medical condition or substance use is also judged to be contributory but is not sufficient to account for a Sexual Disorder (Diagnostic and Statistical Manual of Mental Disorders, 4th edition, Text Revision. Washington D.C., American Psychiatric Association, 2000).

The beneficial effects of the compounds of formula (I) can also be observed regardless of whether the females suffering from above mentioned diseases are in the pre-menopausal, peri-menopausal or post-menopausal state.

As a further feature of the present invention there are provided pharmaceutical compositions comprising as an active ingredient at least one compound of formula (I), as before defined, or a pharmacologically acceptable salt thereof in addition with one or more pharmaceutical carrier, diluents or excipients. For pharmaceutical administration the compounds of general formula (I) and their physiologically acceptable salts may be incorporated into the conventional pharmaceutical preparation in solid, liquid or spray form. The composition may, for example, be presented in a form suitable for oral, rectal, parenteral administration or for nasal inhalation: preferred forms include for example, capsules, tablets, coated tablets, ampoules, suppositories and nasal spray.

The compounds of formula (I), optionally used in form of the pharmacologically acceptable salts thereof, may be incorporated into the conventional pharmaceutical preparation in solid, liquid or spray form. The composition may, for example, be presented in a form suitable for oral, rectal, parenteral administration or for nasal inhalation: preferred forms includes for example, capsules, tablets, coated tablets, ampoules, suppositories and nasal spray.

The active ingredient may be incorporated in excipients or carriers conventionally used in pharmaceutical compositions such as, for example, talc, arabic gum, lactose, gelatine, magnesium stearate, corn starch, aqueous or non aqueous vehicles, polyvynil pyrrolidone, semisynthetic gliceridates of fatty acids, benzalconium chloride, sodium phosphate, EDTA, polysorbate 80.

In case it is desired to further increase the solubilty of the compounds of general formula (I) or of their physiologically acceptable salts, surfactants, non ionic surfactants such as PEG 400, cyclodextrin, metastable polymorphs, inert adsorbents such as bentonite, may be incorporated. Furthermore some techniques may be employed by preparing for example eutectic mixtures and/or solid dispersion by using mannitol, sorbitol, saccharose, succinic acid or physical modified forms by using hydrosoluble polymers, PVP, PEG 4000-20.000.

The compositions are advantageously formulated in dosage units, each dosage unit being adapted to supply a single dose of the active ingredient. The dosis range applicable per day is between 0.1 to 400, preferably between 1.0 to 300, more preferably between 2 to 200 mg.

Each dosage unit may conveniently contain from 0.01 mg to 100 mg, preferably from 0.1 to 50 mg.

The dosage units are administered to the patient 1, 2, 3, or 4 times daily. It is preferred that the compounds of the invention be administered either three or fewer times, more preferably once or twice daily consecutively over a period of time.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The compounds of general formula (I) can be conveniently prepared by a variety of synthetic routes known to those skilled in the art. According to a further object of the present invention, processes for the preparation of compounds of general formula (I) are provided, in which:

a) a compound of general formula (II)

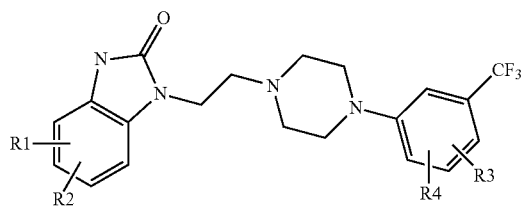

(II)

wherein $R_1$, $R_2$, $R_3$ and $R_4$ denote hydroxy or hydrogen and at least one among $R_1$, $R_2$, $R_3$ and $R_4$ is hydroxy, is reacted with a sulfation reagent such as sulfuric acid, sulfur trioxide, sulfur trioxide in the presence of organic bases or amides or tetrabutyl ammonium hydrogensulfate in combination with dicyclohexylcarbodiimide. The synthesis of the compounds according to formula (II) has been described in WO 01/21593 A1, page 7 line 17 to page 14, line 34.

Preferred reagents are sulfur trioxide in the presence of tertiary amines such as trimethylamine, triethylamine or pyridine, or sulfur trioxide in the presence of dimethylformamide and combinations thereof. Particularly preferred reagent is sulfur trioxide complexed with dimethylformamide in the presence of pyridine. The reaction can be conveniently carried out at temperature ranging from 10 to 50° C. under stirring, preferably between 20 and 50° C., most preferably at 40° C., or b) a compound of general formula (III)

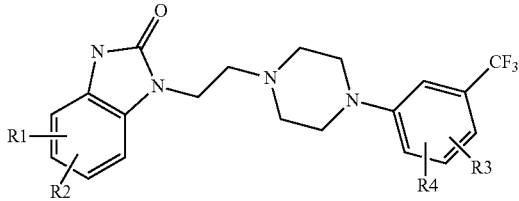

III wherein $R_1$, $R_2$, $R_3$ and $R_4$ denote protected sulfate monoester or hydrogen and at least one among $R_1$, $R_2$, $R_3$ and $R_4$ is a protected sulfate monoester, is reacted with a cleavage reagent to restore the free acid moiety (see: Gunnarson G T et al. Biorganic and Medicinal Chemistry, 13 (2005) 1783-1789; Simpson L S, Journal of the American Chemical Society 128 (2006) 1605-1610). Protecting groups for sulfates are represented by alkyl and halogenated alkyls, preferably isobutyl, neopentyl and 2,2,2-trichloroethyl. In case the protecting group is alkyl, the protected sulfates can be cleaved with nucleophiles in polar aprotic solvents. Examples of nucleophiles are azide, cyanide, iodide and thiocianate; as solvents dimethylformamide and acetone can be conveniently used. The reaction can be conveniently carried out in warm solvents, preferably between 50 and 70° C.

Protected sulfates of general formula (III) can be conveniently prepared by reacting a compound of general formula (II), wherein $R_1$, $R_2$, $R_3$ and $R_4$ denote hydroxy or hydrogen and at least one among $R_1$, $R_2$, $R_3$ and $R_4$ is hydroxy, with suitable alkylchlorosulfates or halogenated alkylchlorosulfates in the presence of a base in an aprotic solvent. Examples of alkylchorosulfates are isobutylchlorosulfate and neopentylchlorosulfate, example of halogenated alkylchlorosulfate is 2,2,2-trichloroethyl chorosulfate. As bases, organic or inorganic bases can be used: non imitative examples are: dimethylaminopyridine, triethylamine, DBU, sodium hydride, sodium bis(trimethylsilyl)amide, etc. As solvent, tetrahydrofurane can be conveniently used.

Alternatively, the compounds of the present invention can be synthesized by enzymatic processes using S9 fractions from human or animal livers as the source of sulfotransferases and adenosine-3'-phosphate-5'-phosphosulfate (PAPS) as the sulphate donor (Foldes A, Meek J L, Biochem. Biophys. Acta 327:365-374, 1973; Honma W et al., drug Metabolism and Disposition 30: 944-949, 2002; Wang Q et al. In Vitro Cell. Dev. Biol.-Animal 41: 97-103, 2005). A typical incubation mixture consists of 100 mM potassium phosphate buffer (pH 7.4), 10 mM magnesium chloride, 1 mM PAPS, human or animal (rat, dog, monkey) liver S9 fraction (commercially available) adjusted to a final protein concentration of 1 mg/mL and of 10-100 µM of a compound of general formula (II) as the substrate. The reaction is initiated by the addition of PAPS and terminated by the addition of 4 times the volume of ice-cold acetonitrile after incubation at 37° C. for 2 to 8 hours depending on the substrate molecule. The mixture is centrifuged to sediment the precipitated protein. The supernatant containing the compound sulphate is concentrated under a stream of nitrogen, re-suspended in water and purified by liquid chromatography using a C18 separating column (100× 4.6 mm ID, ProC18, YMC, Schermbeck, Germany) protected by a guard column (15×4 mm ID, Purosphere E, C18, Merck, Germany) and a flow rate of 1 mL/min. A linear gradient (mobile phase A: 0.1% HCOOH and 10% ACN in water, mobile phase B: 0.1% HCOOH and 75% ACN in water) where ACN concentration increases from 10 to 75% within 25 minutes can be used to separate the sulphate from impurities. The identity of the purified sulphate can be verified by HPLC (mobile phase: 0.1% ammonium formiate, pH 3.3 and 70% acetonitrile in water, 0.3 mL/min flow rate) interfaced to an electrospray (positive) ionization tandem mass spectrometry (API 365, Perkin-Elmer-Sciex, Canada) using a pneumatically assisted electrospray ionisation source. The structure is verified by fragmentation of the [M+H]+ion (m/z 583). The consecutive loss of 2 SO3 moieties (−80 amu, respectively) leads to the key fragment C (m/z 423). At higher collision energies fragment m/z 177 (hydroxylated benzimidazolone sturucture) is also observed.

As mentioned before, the compounds of formula (I) according to the present invention, surprisingly show interesting pharmacological properties owing to their different profile at the serotonine or dopamine receptor subtypes, such as $5\text{-HT}_{1A}$ and $5\text{-HT}_{2A}$. The biochemical profile of the compounds was assessed by evaluating their affinity for the $5\text{-HT}_{1A}$ and $5\text{-HT}_{2A}$ receptors, according to the methods described below.

Receptor Binding Studies

Binding studies can be carried out to determine the affinity of the compounds for $5\text{-HT}_{1A}$ and $5\text{-HT}_{2A}$ receptors $5\text{-HT}_{1A}$ Receptor Human recombinant CHO-K1 cells are used. Displacement experiments can be performed by incubating the cells in 50 mM Tris-HCL, pH 7.4, 0.1% ascorbic acid, 0.5 mM EDTA, 10 mM MgSo4 and in the presence of [$^3$H]-8-OH-DPAT (1.5 nM) at 27° C. for 60 min. Non specific binding was determined in the presence of 10 µM mertergoline.

The test compounds dissolved in DMSO, along with the positive control compound metergoline are tested over 10-log unit concentrations for their ability to compete for [$^3$H]8-OH-DPAT binding (May J A, et al., J Pharmacol Exp Ther. 306 (1):301, 2003. Martin G R and Humphrey P P A Neuropharmacol. 33:261, 1994). The assays are terminated by rapid vacuum filtration over glass fiber filters. The radioactivity is counted on a β-counter, and the data are analyzed by a non-linear, iterative, curve-fitting computer program.

Where presented, IC50 values are determined by a non-linear, least squares regression analysis using Data Analysis Toolboxä (MDL Information Systems, San Leandro, Calif., USA). Where inhibition constants (Ki) are presented, the Ki values are calculated using the equation of Cheng and Prusoff (Cheng, Y., Prusoff, W. H., Biochem. Pharmacol. 22:3099-3108, 1973) using the observed IC50 of the tested compound, the concentration of radioligand employed in the assay, and the historical values for the Ki of the ligand).

$5\text{ HT}_{2A}$ Receptor

Human recombinant CHO-K1 cells can be used. Displacement experiments are performed by incubating the cells in 50 mM Tris-HCL, pH 7.7 in the presence of [$^3$H]-Ketanserin (0.5 nM) at 25° C. for 60 min. Non specific binding was determined in the presence of 1 µM Mianserin.

The test compounds, along with the positive control compound ketanserin are tested over 10-log unit concentrations for their ability to compete for [$^3$H]-Ketanserin (Saucier C and Albert P R. J. Neurochem. 68:1998, 1997. Bonhaus D W et al., Br J Pharmacol. 115:622, 1995). The assays are terminated by rapid vacuum filtration over glass fiber filters. The radioactivity is counted on a β-counter, and the data are analyzed by a nonlinear, iterative, curve-fitting computer program. Where presented, IC50 values are determined by a non-linear, least squares regression analysis using Data Analysis Toolboxä (MDL Information Systems, San Leandro, Calif., USA). Where inhibition constants (Ki) are presented, the Ki values are calculated using the equation of Cheng and Prusoff (Cheng, Y., Prusoff, W. H., Biochem. Pharmacol. 22:3099-3108, 1973) using the observed IC50 of the tested compound, the concentration of radioligand employed in the assay, and the historical values for the Ki of the ligand).

The following table (Table I) collects the affinity values (Ki, nM) at the said receptors of the new compounds.

TABLE I

| Ki (nM) for $5\text{-HT}_{1A}$ and $5\text{-HT}_{2A}$ receptors | | |
|---|---|---|
| Compound | $5\text{-HT}_{1A}$ | $5\text{-HT}_{2A}$ |
| I(b) | 808 | 207 |

Experimental Part

The following examples illustrate the preparation of compounds according to the invention. It should be understood that the invention is not limited to the given examples of chemical methods and processes for the preparation of the substances, as other conventional methods well known to those skilled in the art, are suitable too.

EXAMPLE 1

{2-oxo-3-{2-[4-(3-trifluoromethyl-phenyl)-piperazin-1-yl]-ethyl}-2,3-dihydro-1H-benzimidazol-5-yl}mono sulfuric acid ester 6-Hydroxy-1-{2-[4-(3-trifluoromethyl-phenyl)-piperazin-1-yl]-ethyl}-1,3-dihydro-benzimidazol-2-one (2.0 g; 4.9 mmol) is dissolved in pyridine (10 ml) in a round bottom flask under stirring. Sulfur trioxide dimethylformamide complex (3.8 g, 24.2 mmol) dissolved in pyridine (4 ml) is added at room temperature; then the mixture is warmed to 40° C. until a suspension is formed.

The reaction mixture is evaporated under vacuum to remove most of the liquid. The almost solid residue is taken up in 1:1 mixture of ethylether and ethylacetate, then triturated and filtered through fritted glass. The residual solid is repeatedly washed with water and finally with ethyl ether. Upon drying, the title compound is obtained as solid, 1.48 g; m.p. 262-264° C.

The other sulfates can be prepared by the outlined procedure from the corresponding hydroxy derivatives described in WO 01/21593 A1 on page 2 line 13 to 29. Those hydroxy derivatives can be synthesized as described in WO 01/21593 A1, page 7 line 17 to page 14, line 34.

EXAMPLE 2

5-Methoxy-1-{2-[4-(4-methoxy-3-trifluoromethyl-phenyl)piperazin-1-yl]-ethyl}-1,3-dihydro-benzimidazol-2-one i) N-(4-Methoxy-2-nitro-phenyl)-2-[4-(4-methoxy-3-trifluoromethyl-phenyl)-piperazin-1-yl]acetamide 2-Bromo-N-(4-methoxy-2-nitro-phenyl)-acetamide (6.7 g; 19.6 mmol) is dissolved in 200 ml ethanol in the presence of 6.3 g sodium carbonate. 1-(4-Methoxy-3-trifluoromethyl-phenyl)-piperazine hydrochloride (5.8 g; 19.6 mmol) is added to the resulting suspension and the mixture is stirred overnight at room temperature. The mixture is evaporated to dryness under vacuum and the residue is taken up with water and ethylacetate. The organic phase is separated and washed twice with water. After drying over magnesium sulfate, evaporation of the solvent leaves a residue which is triturated with ethylether.

ii) 2-Amino-4-methoxy-N-{2-[4-(4-methoxy-3-trifluoromethyl-phenyl)piperazin-1-yl]-ethyl}-aniline N-(4-Methoxy-2-nitro-phenyl)-2-[4-(4-methoxy-3-trifluoromethyl-phenyl)-piperazin-1-yl]acetamide (6.1 g; 11 mmol) iss dissolved in 70 ml tetrahydrofurane. Borane-tetrahydrofurane complex (90 ml of 1M THF solution) is added at 10° C. and the mixture is warmed to 55° C. for 4 hours. After cooling to room temperature, the solvent is evaporated under vacuum and the residue is taken with ethanol and acidified with hydrochloric acid. Heating to 50° C. takes place for 60 min. Upon overnight cooling, the unreacted compound is separated by filtration. The liquid phase is dried under vacuum, taken up with water and, after removal of the undissolved solid, saturated sodium hydrogencarbonate solution is added. The aqueous phase is extracted with ethylacetate and the organic layer is dessicated prior to evaporation. The residue is purified by silicagel chromatography (methylene chloride/methanol/32% aqueous ammonia 95:5:0.5). The title compound can be directly used for the following step.

iii) 5-Methoxy-1-{2-[4-(4-methoxy-3-trifluoromethyl-phenyl)piperazin-1-yl]-ethyl}-1,3-dihydro-benzimidazol-2-one 2-Amino-4-methoxy-N-{2-[4-(4-methoxy-3-trifluoromethyl-phenyl)piperazin-1-yl]-ethyl}-aniline (2.5 g, 6 mmol) is dissolved in 30 ml tetrahydrofurane; 1.5 g (9 mmol) carbonyldiimidazole is added portionwise to the resulting solution. The mixture is left at room temperature under stirring for 24 h. After evaporation to dryness, the residue is purified by silicagel chromatography (methylene chloride/methanol/32% aqueous ammonia 95:5:0.5). The crude title compound is triturated with ethylether.

EXAMPLE 3

1-{2-[4-(2-Methoxy-5-trifluoromethyl-phenyl)-piperazin-1-yl]-ethtl}-1,3-dihydro-benzimidazol-2-one 1-(2-methoxy-5-trifluoromethyl-phenyl)-piperazine hydrochloride (1.2 g; 4.0 mmol) and 1-(2-chloroethyl)-1,3-dihydro-benzimidazol-2-one (0.81 g; 4.2 mmol) are dissolved in 10 ml dimethylformamide in the presence of 0.56 g potassium carbonate. The mixture is heated to 100° C. for 8 hours. After cooling, it is partitioned between 50 ml water and 30 ml ethylacetate; the aqueous phase is extracted once more with ethylacetate. The organic layer is washed with 5% hydrochloric acid and with water. The organic layer is dried and evaporated under vacuum. The residue is triturated with ethylacetate.

The deprotection of the hydroxy groups of the compounds described in Example 2) and 3) can easily carried out by conventional known procedures e.g. as described in WO 01/21593 A1. For example, the deprotection can be achieved by treatment with strong aqueous acids such as 48% hydrobromic acid at high temperatures or alternatively by treatment with boron derivatives such as $BBr_3$, at low temperatures in chlorurated solvents such as methylene chloride. The resulting deprotected hydroxy-derivatives can be easily converted to the corresponding disulfate ester as described in Example 1.

EXAMPLES OF PHARMACEUTICAL FORMULATIONS

| A) Tablets | per tablet |
|---|---|
| compound (I.a) | 100 mg |
| lactose | 240 mg |
| corn starch | 340 mg |
| polyvinylpyrrolidone | 45 mg |
| magnesium stearate | 15 mg |
| | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| compound (I.b) | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| compound (I.c) | 5 mg |
| corn starch | 41.5 mg |
| lactose | 30 mg |
| polyvinylpyrrolidone | 3 mg |
| magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) Capsules | per capsule |
|---|---|
| compound (I.d) | 150 mg |
| Corn starch | 268.5 mg |
| Magnesium stearate | 1.5 mg |
| | 420 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| compound (I.e) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion.

| F) Suppositories | |
|---|---|
| compound (I.f) | 50 mg |
| solid fat | 1650 mg |
| | 1700 mg |

The hard fat is melted. At 40° C. the ground active substance is homogeneously dispersed. It is cooled to 38° C. and poured into slightly chilled suppository moulds.

The invention claimed is:

1. A compound of formula (I)

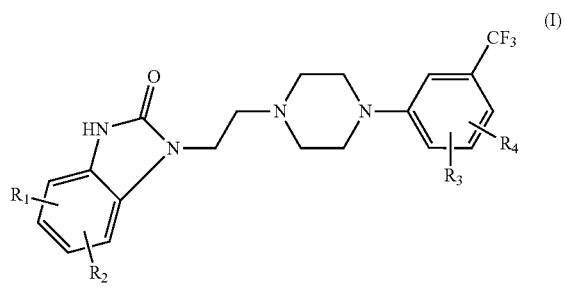

(I)

wherein $R_1$, $R_2$, $R_3$, and $R_4$ are each hydrogen or sulfate monoester with the proviso that $R_1$, $R_2$, $R_3$, and $R_4$ cannot simultaneously be hydrogen, or a pharmacologically acceptable salt thereof.

2. The compounds of formula (I) according to claim 1 wherein two or three of the four radicals $R_1$, $R_2$, $R_3$, and $R_4$ are hydrogen.

3. The compound according to claim 1, selected from the group consisting of;

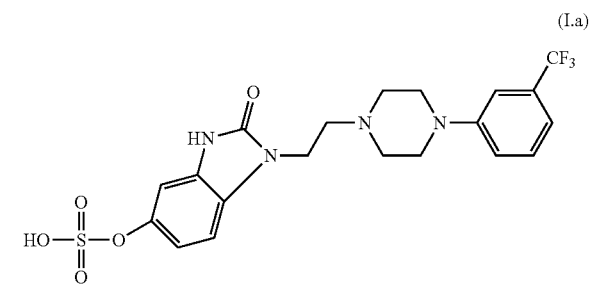

(I.a)

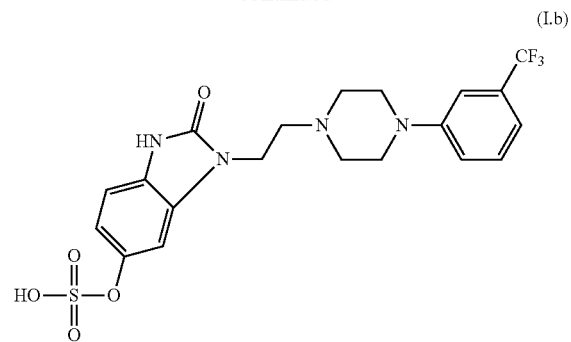
(I.b)
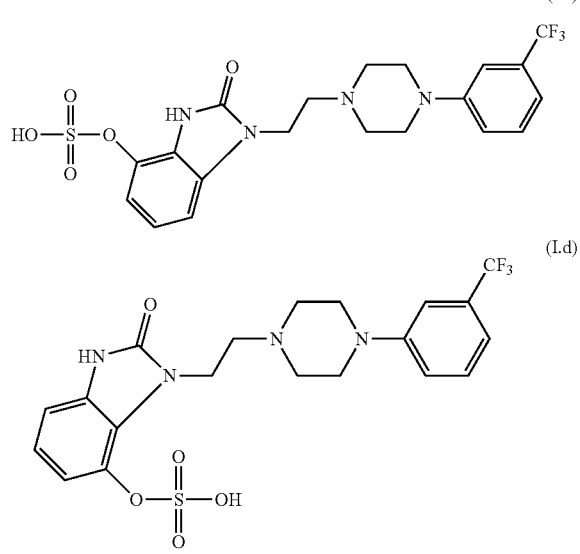
(I.c)
(I.d)
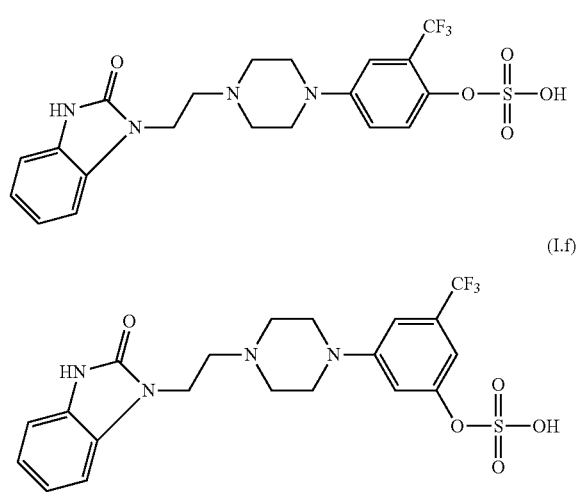
(I.e)
(I.f)
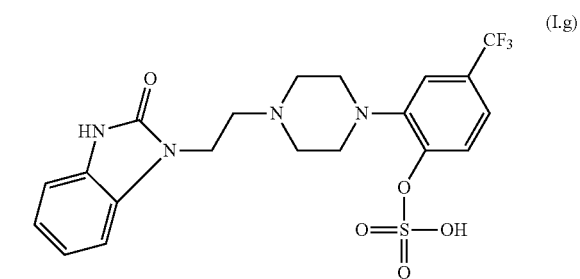
(I.g)
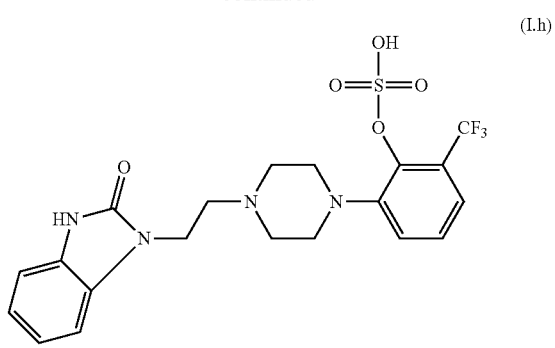
(I.h)
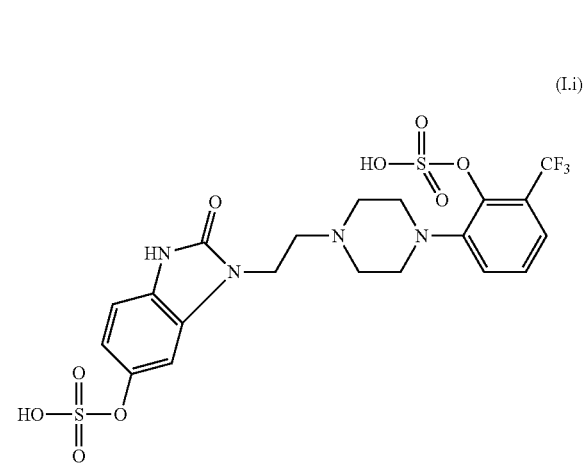
(I.i)
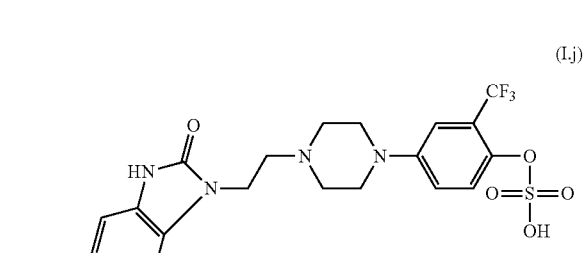
(I.j)
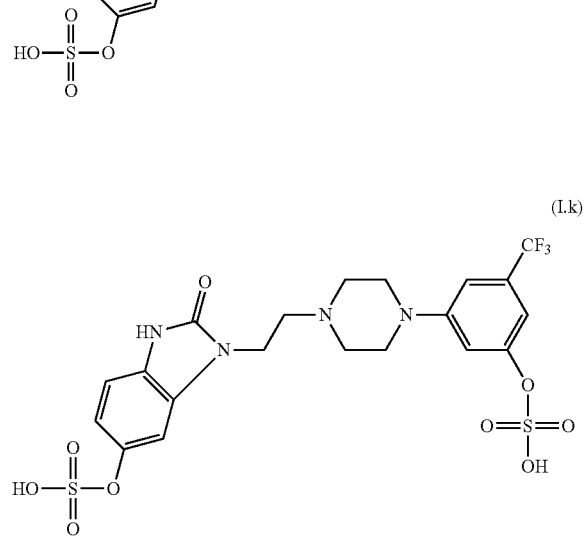
(I.k)

-continued (I.1)

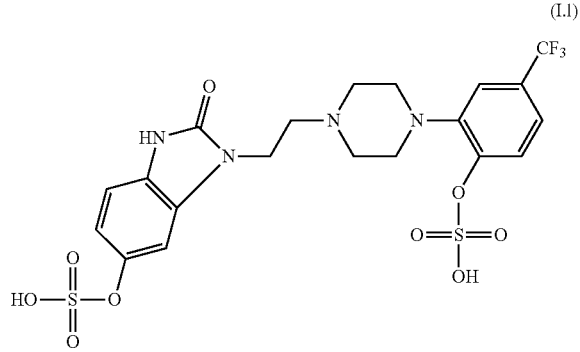

or a pharmacologically acceptable salt thereof.

4. A process for the preparation of a compound of formula (I) according to one of claims 1 to 3, wherein a compound of formula (II)

(II)

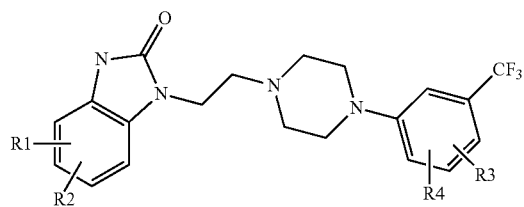

wherein $R_1$, $R_2$, $R_3$ and $R_4$ are each hydroxy or hydrogen and at least one among $R_1$, $R_2$, $R_3$ and $R_4$ is hydroxy, is reacted with a sulfation reagent.

5. A process for the preparation of compound of formula (I) according to one of claims 1 to 3, wherein a compound of formula (III)

(III)

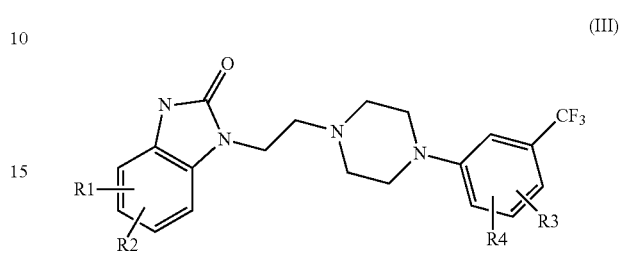

wherein $R_1$, $R_2$, $R_3$, and $R_4$ are each a protected sulfate monoester or hydrogen and at least one among $R_1$, $R_2$, $R_3$, and $R_4$ is a protected sulfate monoester, is reacted with a cleavage reagent to restore the free acid moiety of the sulfate monoester group.

6. A pharmaceutical composition comprising a compound of formula (I) according to one of claims 1 to 3, or a pharmacologically acceptable salt thereof, in admixture with one or more pharmaceutical carriers, diluents or excipients.

* * * * *